United States Patent [19]

Takaya et al.

[11] 4,409,217
[45] Oct. 11, 1983

[54] CEPHEM COMPOUNDS

[75] Inventors: Takao Takaya, Kawanishi; Hisashi Takasugi, Kohamanishi; Toshiyuki Chiba; Kiyoshi Tsuji, both of Osaka, all of Japan

[73] Assignee: Fujisawa Pharmaceutical Co., Ltd., Osaka, Japan

[21] Appl. No.: 190,970

[22] Filed: Sep. 26, 1980

Related U.S. Application Data

[63] Continuation-in-part of Ser. No. 886,340, Mar. 14, 1978.

[51] Int. Cl.³ .................. A61K 31/545; C07D 501/59
[52] U.S. Cl. ......................................... 424/246; 544/22
[58] Field of Search ........................... 544/22; 424/246

[56] References Cited

U.S. PATENT DOCUMENTS

| | | | |
|---|---|---|---|
| 4,166,115 | 8/1979 | Takaya et al. | 544/27 |
| 4,278,793 | 7/1981 | Durckheimer et al. | 544/22 |

FOREIGN PATENT DOCUMENTS

| | | |
|---|---|---|
| 866038 | 10/1978 | Belgium . |
| 2805655 | 8/1978 | Fed. Rep. of Germany . |
| 2810922 | 9/1978 | Fed. Rep. of Germany . |
| 2812625 | 9/1978 | Fed. Rep. of Germany . |
| 2912829 | 10/1979 | Fed. Rep. of Germany ........ 544/22 |

*Primary Examiner*—Paul M. Coughlan, Jr.
*Attorney, Agent, or Firm*—Oblon, Fisher, Spivak, McClelland & Maier

[57] ABSTRACT

The invention relates to new cephem compounds, of high antimicrobial activity of the formula:

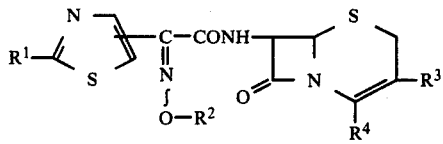

wherein
$R^1$ is amino or protected amino,
$R^2$ is carboxy(lower)alkyl or protected carboxy(lower)alkyl,
$R^3$ is halogen or lower alkoxy, and
$R^4$ is carboxy or protected carboxy,
and a pharmaceutically acceptable salt thereof.

3 Claims, No Drawings

CEPHEM COMPOUNDS

This application is a Continuation-In-Part of parent application Ser. No. 886,340, filed Mar. 14, 1978.

The present invention relates to new cephem compounds and pharmaceutically acceptable salts thereof. More particularly, it relates to new cephem compounds and pharmaceutically acceptable salts thereof, which have antimicrobial activities, to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula:

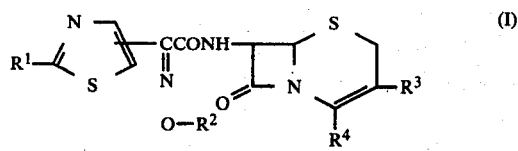

wherein
 $R^1$ is amino or protected amino,
 $R^2$ is carboxy(lower)alkyl or protected carboxy(lower)alkyl,
 $R^3$ is halogen or lower alkoxy, and
 $R^4$ is carboxy or protected carboxy.

According to the present invention, the new cephem compounds (I) can be prepared by various processes which are illustrated in the following schemes.

Process 1

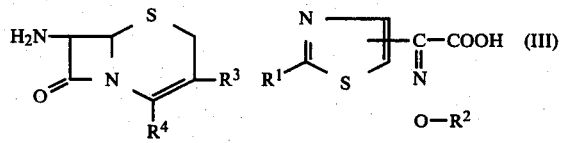

(II)

or its reactive derivative at the amino group or a salt thereof or its reactive derivative at the carboxy group or a salt thereof

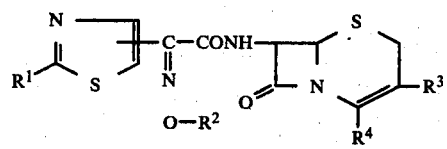

(I)

or a salt thereof

Process 2

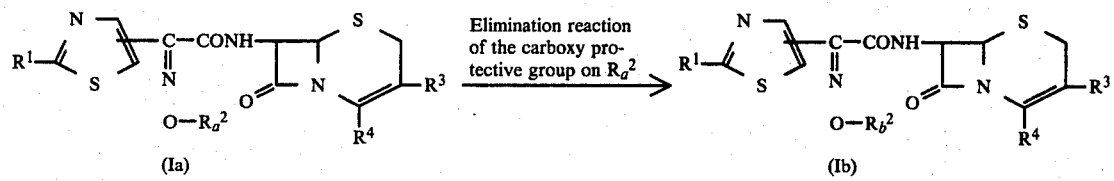

(Ia)

or a salt thereof

Elimination reaction of the carboxy protective group on $R_a{}^2$ (Ib)

or a salt thereof

Process 3

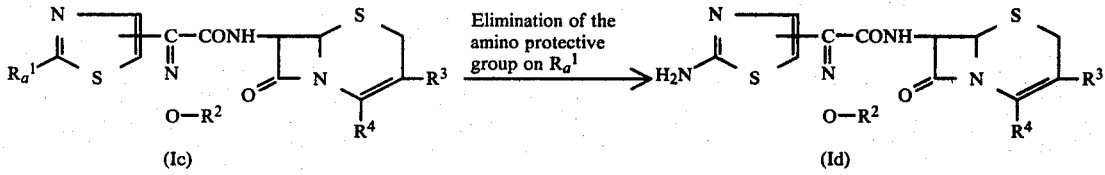

(Ic)

or a salt thereof

Elimination of the amino protective group on $R_a{}^1$ (Id)

or a salt thereof

Process 4

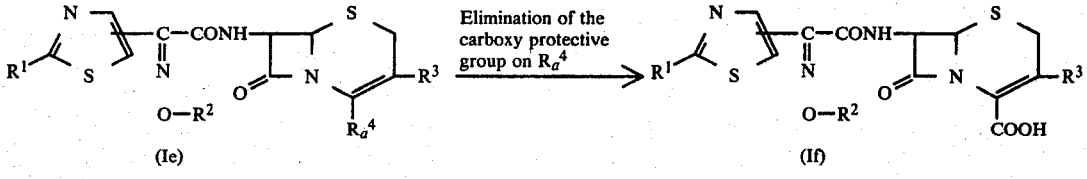

(Ie)

or a salt thereof

Elimination of the carboxy protective group on $R_a{}^4$ (If)

or a salt thereof wherein
R$^1$, R$^2$, R$^3$ and R$^4$ are each as defined above,
R$_a^1$ is protected amino,
R$_a^2$ is protected carboxy(lower)alkyl,
R$_b^2$ is carboxy(lower)alkyl, and
R$_a^4$ is protected carboxy.

Regarding the object compounds (I), (Ia), (Ib), (Ic), (Id), (Ie), (If) and the starting compound (III), it is to be understood that said object and starting componds include syn isomer, anti isomer and a mixture thereof. For example, with regard to the object compound (I), syn isomer means one geometrical isomer having the partial structure represented by the following formula:

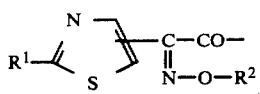

(wherein R$^1$ and R$^2$ are each as defined above) and anti isomer means the other geometrical isomer having the partial structure represented by the following formula:

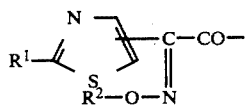

(wherein R$^1$ and R$^2$ are each as defined above).

Suitable pharmaceutically acceptable salts of the object compounds (I) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, sulfate, phosphate, etc.), or a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable "protected amino" may include an acylamino or an amino group substituted by a conventional protecting group such as ar(lower)alkyl which may have at least one suitable substituent(s), (e.g. benzyl, trityl, etc.) or the like.

Suitable acyl moiety in the terms "acylamino" may include aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbonyl, propoxycarbonyl, 1-cyclopropylethoxycarbonyl, isopropoxycarbonyl, butoxycarbonyl, tert-butoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.); arenesulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.), and the like. The acyl moiety as stated above may have at least one suitable substituent(s) such as halogen (chlorine, bromine, fluorine and iodine) or the like.

Preferable examples of acylamino may include lower alkanoylamino.

Suitable "protected carboxy" and "protected carboxy moiety" in the term "protected carboxy(lower)alkyl" may include an esterified carboxy and the like, and suitable examples of the ester moiety in said esterified carboxy may be the ones such as lower alkyl ester (e.g. methyl ester, ethyl ester, propyl ester, isopropyl ester, butyl ester, isobutyl ester, pentyl ester, hexyl ester, 1-cyclopropylethyl ester, etc.) which may have at least one suitable substituent(s), for example, lower alkanoyloxy(lower)alkyl ester (e.g. acetoxymethyl ester, propionyloxymethyl ester, butyryloxymethyl ester, valeryloxymethyl ester, pivaloyloxymethyl ester, 2-acetoxyethyl ester, 2-propionyloxyethyl ester, hexanoyloxymethyl ester, etc.), lower alkanesulfonyl(lower)alkyl ester (e.g. 2-mesylethyl ester, etc.) or mono(or di or tri)-halo(lower)alkyl ester, (e.g. 2-iodoethyl ester, 2,2,2-trichloroethyl ester, etc.); lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.), and the like.

Preferable examples of the esterified carboxy as mentioned above may include lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.) and phenyl(lower)alkoxycarbonyl (e.g. benzyloxycarbonyl, diphenylmethoxycarbonyl, etc.) which may have a nitro group.

Suitable "lower alkyl moiety" in the terms "carboxy(lower)alkyl" and "protected carboxy(lower)alkyl" may include methyl, ethyl, propyl, isopropyl, butyl, t-butyl, pentyl, hexyl and the like.

Preferable examples of carboxy(lower)alkyl may include carboxymethyl, 1-carboxyethyl, 2-carboxyethyl, 1-carboxypropyl, 2-carboxypropyl, 3-carboxypropyl, 4-carboxybutyl, 5-carboxypentyl, 6-carboxyhexyl, 1-carboxyisopropyl, 1-ethyl-1-carboxyethyl, 2-methyl-2-carboxypropyl, and the like.

Preferable examples of protected carboxy(lower)alkyl may include esterified carboxy(lower)alkyl, and more preferably lower alkoxycarbonyl(lower)alkyl (e.g. methoxycarbonylmethyl, ethoxycarbonylmethyl, propoxycarbonylmethyl, tert-butoxycarbonylmethyl, 2-ethoxycarbonylethyl, 2-ethoxycarbonylpropyl, 4-ethoxycarbonylbutyl, 1-tert-butoxycarbonylisopropyl, 1-tert-butoxycarbonyl-1-methylpropyl, 4-tert-butoxycarbonylbutyl, 5-tert-butoxycarbonylpentyl, 6-butoxycarbonylhexyl, etc.) and the like.

Suitable "halogen" may include chlorine, bromine or iodine, and preferably chlorine or bromine.

Suitable "lower alkoxy" may include methoxy, ethoxy, propoxy, isopropoxy, butoxy, pentyloxy, hexyloxy and the like, and preferably methoxy.

The processes for preparing the object compounds of the present invention are explained in details in the following.

PROCESS 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide or the like; a derivative formed by reaction of the compound (II) with phosphorus trichloride or phosgene, and the like.

Suitable salt of the compounds (II) and (III) may include an acid addition salt such as an organic acid salt (e.g. acetate, maleate, tartrate, benzenesulfonate, toluenesulfonate, etc.) or an inorganic acid salt (e.g. hydrochloride, hydrobromide, sulfate, phosphate, etc.); a metal salt (e.g. sodium salt, potassium salt, calcium salt, magnesium salt, etc.); ammonium salt; an organic amine salt (e.g. triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorus acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methyl imidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

In the present reaction, a syn isomer of the object compound (I) can be obtained preferably by conducting the present invention of the compound (II) with the corresponding syn isomer of the starting compound (III), for example, in the presence of a Vilsmeier reagent as mentioned above etc. and under around neutral condition.

PROCESS 2

The object compound (Ib) or a salt thereof can be prepared by subjecting the compound (Ia) or a salt thereof to elimination reaction of the carboxy protective group on $R_a^2$.

Suitable salt of the compound (Ia) can be referred to the one exemplified for the compound (I).

The present elimination reaction can be carried out in a similar manner to that of aftermentioned Process 4.

The present invention includes, within its scope, the cases that another protected carboxy and/or protected amino group(s) are converted into the corresponding free carboxy and/or amino group(s) during the reaction or the post-treating step of the present process.

PROCESS 3

The object compound (Id) or a salt thereof can be prepared by subjecting the compound (Ic) or a salt thereof to elimination reaction of the amino protective group on $R_a^1$.

Suitable salt of the compound (Ic) can be referred to the metal salt, ammonium salt and organic amine salt exemplified for the compound (II).

The elimination reaction is carried out in accordance with a conventional method such as hydrolysis; reduction; a method treating the compound (Ic) wherein $R_a^1$ is acylamino with iminohalogenating agent, iminoetherifying agent and then, if necessary, hydrolyzing the resultant; or the like. The hydrolysis may include a method using an acid or base or hydrazine and the like. These methods may be selected depending on the kind of the protective groups to be eliminated.

Among these methods, hydrolysis using an acid is one of the most common and preferable method for eliminating the protective groups such as substituted or unsubstituted alkoxycarbonyl, for example, tert-pentyloxycarbonyl, lower alkanoyl (e.g. formyl, acetyl, etc.), cycloalkoxycarbonyl, substituted or unsubstituted aralkoxycarbonyl, aralkyl (e.g. trityl), substituted phenylthio, substituted aralkylidene, substituted alkylidene, substituted cycloalkylidene or the like.

Suitable acid includes an organic or inorganic acid such as formic acid, trifluoroacetic acid, benzenesulfonic acid, p-toluenesulfonic acid, hydrochloric acid and the like, and the most suitable acid is an acid which can easily be removed from the reaction mixture by a conventional manner such as distillation under reduced pressure, for example, formic acid, trifluoroacetic acid, hydrochloric acid, etc. The acids can be selected according to the kind of the protective group to be eliminated. When the elimination reaction is conducted with an acid, it can be carried out in the presence or absence of a solvent. Suitable solvent includes water, a conventional organic solvent or a mixture thereof.

The elimination reaction using trifluoroacetic acid may be carried out in the presence of anisole. The hydrolysis using hydrazine is commonly applied for eliminating a phthaloyl, succinyl type amino-protective group.

The elimination using base is used for eliminating an acyl group such as trifluoroacetyl. Suitable base may include an inorganic base and an organic base.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, etc.), 2-pyridylmethoxycarbonyl, etc. Suitable reduction may include, for example, reduction with an alkali metal borohydride (e.g. sodium borohydride, etc.), reduction with a combination of a metal (e.g. tin, zinc, iron, etc.) or the said metal together with a metal salt compound (e.g. chromous chloride, chromous acetate, etc.) and an organic or inorganic acid (e.g. acetic acid, propionic acid, hydrochloric acid, etc.); and catalytic reduction. Suitable catalyst includes a conventional one, for example, Raney nickel, platinum oxide, palladium carbon and the like.

Among the protective groups, the acyl group can generally be eliminated by hydrolysis. Especially, halogen substituted-alkoxycarbonyl and 8-quinolyloxycarbonyl groups are usually eliminated by treating with a heavy metal such as copper, zinc, or the like.

Among the protective groups, the acyl group can also be eliminated by treating with an iminohalogenating agent (e.g. phosphorus oxychloride, etc.) and an iminoetherifying agent such as lower alkanol (e.g. methanol, ethanol, etc.), if necessary, followed by hydrolysis.

The reaction temperature is not critical and may suitably be selected in accordance with the kind of the amino protective group and the elimination method as mentioned above, and the reaction is preferably carried out under a mild condition such as under cooling or at slightly elevated temperature.

The present invention includes, within its scope, the cases that another protected amino and/or protected carboxy group(s) are converted into the corresponding free amino and/or the free carboxy group(s) during the reaction or the post-treating step of the present process.

PROCESS 4

The object compound (If) or a salt thereof can be prepared by subjecting the compound (Ie) or a salt thereof to elimination reaction of the carboxy protective group on $R_a^4$.

Suitable salt of the compound (Ie) can be referred to the acid addition salt exemplified for the compound (II).

In the present elimination reaction, all conventional methods used in the elimination reaction of the carboxy protective group, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the presence of a base or an acid. Suitable base may include an inorganic base and an organic base as aforementioned.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and it may suitably be selected in accordance with the kind of the carboxy protective group and the elimination method.

The elimination using Lewis acid is preferable to eliminate substituted or unsubstituted ar(lower)alkyl ester and carried out by reacting the compound (Ie) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), diethyl ether, carbon disulfide or any other solvent which does not adversely affect the reaction. These solvents may be used as a mixture thereof. The reaction temperature is not critical, and the reaction is usually carried out under cooling, at ambient temperature or under warming.

The reductive elimination can be applied preferably for elimination of the protective group such as halo(lower)alkyl (e.g. 2-iodoethyl, 2,2,2-trichloroethyl, etc.) ester, ar(lower)alkyl (e.g. benzyl, etc.) ester or the like. The reduction method applicable for the elimination reaction may include, for example, reduction by using a combination of a metal (e.g. zinc, zinc amalgam, etc.) or a salt of chromium compound (e.g. chromous chloride, chromous acetate, etc,) and an organic or inorganic acid (e.g. acetic acid, propionic acid, hydrochloric acid, etc.); and conventional catalytic reduction in the presence of a conventional metallic catalyst (e.g. palladium carbon, Raney nickel, etc.).

The present elimination reaction of the carboxy protective group includes, within its scope, the cases that protected amino group in the compound (Ie) is transformed into free amino group according to reaction conditions and kinds of the protective groups in the course of the reaction and/or in post-treatment of the reaction.

The present invention includes, within its scope, the cases that the one type of tautomeric isomers is converted into the other type of isomer during the reaction and/or the post-treating step of the each process.

In case that the object compound (I) is obtained in a form of the free acid at the 4-position and/or the oxime portion and/or in case that the compound (I) has free amino group, it may be transformed into its pharmaceutically acceptable salt as aforementioned by a conventional method.

The object compounds (I) and pharmaceutically acceptable salt thereof of the present invention are novel compounds which exhibit high antibacterial activity and inhibit the growth of a wide variety of pathogenic microorganisms including Gram-positive and Gram-negative bacteria. For therapeutic purpose, the compounds according to the present invention can be used in the form of pharmaceutical preparation which contain said compounds, as an active ingredient, in admixture with a pharmaceutically acceptable carriers such as an organic or inorganic solid or liquid excipient suitable for oral, parenteral or external administration. The pharmaceutical preparations may be capsules, tablets, dragees, ointments or suppositories, solutions, suspensions, emulsions, and the like. If desired, there may be included in the above preparations auxiliary substances, stabilizing agents wetting or emulsifying agents, buffers and other commonly used additives.

While the dosage of the compounds will vary depend upon the age and condition of the patient, an average single dose of about 10 mg., 50 mg., 100 mg, 250 mg., 500 mg., and 1000 mg. of the compounds according to the present invention was proved to be effective for treating infectious diseases caused by pathogenic bacteria. In general, amounts between 1 mg/body and about 6,000 mg/body or even more may be administered per day.

In order to illustrate the usefulness of the object compound, anti-microbial activities of some representative compounds of the present invention against some test strains of pathogenic bacteria are shown in their minimal inhibitory concentrations below.

TEST METHOD

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in terms of μg/ml. after incubation at 37° C. for 20 hours.

Test compound
(1) 7-[2-carboxymethoxyimino-2-(2-aminothiazol-4-yl)acetamido]-3-chloro-3-cephem-4-carboxylic acid (syn isomer).

| Test results | |
|---|---|
| Test Microorganisms | M.I.C. (μg/ml) Compound (1) |
| Proteus vulgaris IAM-1025 | 0.1 |
| Escherichia coli NIHJ JC-2 | 0.39 |

| Test results | |
|---|---|
| Test Microorganisms | M.I.C. (μg/ml) Compound (1) |
| Klebsiella pneumoniae 7 | 0.05 |
| Proteus mirabilis 1 | 0.025 |
| Escherichia cloacae 60 | 25.0 |

The following Examples are given for the purpose of illustrating the present invention in more detail.

EXAMPLE 1

Dry tetrahydrofuran (20 ml) and 2-(tert-butoxycarbonylmethoxyimino)-2-(2-formamidothiazol-4-yl)acetic acid (syn isomer, 2.1 g) were added to a Vilsmeier reagent, which was prepared from dry N,N-dimethylformamide (0.6 g), dry ethyl acetate (2.4 ml) and phosphorus oxychloride (1.4 g) in an usual manner, and the resulting mixture was stirred at −3° to 3° C. for 30 minutes to give a solution containing the activated acid.

Dry ethyl acetate (50 ml) and N-(trimethylsilyl)acetamide (5.4 g) were added to 4-nitrobenzyl 7-amino-3-chloro-3-cephem-4-carboxylate hydrochloride (2.5 g), and stirred at 40° C. for 20 minutes. To the solution was added the solution containing the activated acid at −10° C. and stirred at −10° to −5° C. for 30 minutes. Water (40 ml) was added to the resultant solution and allowed to stand at room temperature. The organic layer was separated, washed with a saturated solution of sodium bicarbonate twice and saturated solution of sodium chloride subsequently, and dried over magnesium sulfate. The solution was concentrated to dryness and triturated with diisopropyl ether. The precipitates were collected by filtration and dried to give 4-nitrobenzyl 7-[2-(tert-butoxycarbonylmethoxyimino)-2-(2-formamidothiazol-4-yl)acetamido]-3-chloro-3-cephem-4-carboxylate (syn isomer, 3.9 g).

IR (Nujol): 1780, 1730, 1680, 1640 cm$^{-1}$.

NMR (DMSO-d$_6$, δ): 1.45 (9H, s), 3.93 (2H, q, J=16.0 Hz), 4.63 (2H, s), 5.26 (1H, d, J=5.0 Hz), 5.48 (2H, s), 5.96 (1H, dd, J=5.0 Hz, 8.0 Hz), 7.45 (1H, s), 7.72 (2H, d, J=9.0 Hz), 8.28 (2H, d, J=9.0 Hz), 8.55 (1H, s), 9.72 (1H, d, J=8.0 Hz).

EXAMPLE 2

4-Nitrobenzyl 7-amino-3-methoxy-3-cephem-4-carboxylate hydrochloride (4.02 g) and 2-(tert-butoxycarbonylmethoxyimino)-2-(2-formamidothiazol-4-yl)acetic acid (syn isomer, 3.62 g) were treated in a similar manner to to that of Example 1 to give 4-nitrobenzyl 7-[2-(tert-butoxycarbonylmethoxyimino)-2-(2-formamidothiazol-4-yl)acetamido]-3-methoxy-3-cephem-4-carboxylate (syn isomer, 6.8 g).

IR (Nujol): 3400–3150, 1770, 1720, 1680, 1600, 1530 cm$^{-1}$.

NMR (DMSO-d$_6$, δ): 1.46 (9H, s), 3.70 (2H, broad s), 3.86 (3H, s), 4.66 (2H, s), 5.26 (1H, d, J=5 Hz), 5.36 (2H, m), 5.70 (1H, d,d, J=5,8 Hz), 7.53 (1H, s), 7.65 (2H, d, J=8 Hz), 8.20 (2H, d, J=8 Hz), 8.50 (1H, s), 9.56 (1H, d, J=8 Hz).

EXAMPLE 3

Methanol (40 ml), tetrahydrofuran (20 ml) and acetic acid (0.3 ml) were added to 4-nitrobenzyl 7-[2-(tert-butoxycarbonylmethoxyimino)-2-(2-formamidothiazol-4-yl)acetamido]-3-chloro-3-cephem-4-carboxylate (syn isomer, 3.8 g). 10% Palladium carbon (1.9 g) containing water (3 ml) was added to the solution, and subjected to catalytic reduction for 4 hours. After removal of palladium carbon by filtration, the filtrate was concentrated in vacuo. To the residue were added ethyl acetate and water, and the solution was adjusted to pH 7.5 with a saturated solution of sodium bicarbonate. After the aqueous layer was separated, ethyl acetate was added to the aqueous layer, and adjusted to pH 2.0 with 10% hydrochloric acid. The ethyl acetate layer was separated. The organic solution was washed with a saturated solution of sodium chloride, dried over magnesium sulfate and concentrated in vacuo. The residue was triturated with diisopropyl ether, and then the precipitates were collected by filtration and dried to give 7-[2-(tert-butoxycarbonylmethoxyimino)-2-(2-formamidothiazol-4-yl)acetamido]-3-chloro-3-cephem-4-carboxylic acid (syn isomer, 2.31 g).

IR (Nujol): 3160, 1780, 1720, 1670 cm$^{-1}$.

EXAMPLE 4

4-Nitrobenzyl 7-[2-(tert-butoxycarbonylmethoxyimino)-2-(2-formamidothiazol-4-yl)acetamido]-3-methoxy-3-cephem-4-carboxylate (syn isomer, 6.8 g), methanol (60 ml) tetrahydrofuran (60 ml), acetic acid (6 ml), water (10 ml) and 10% palladium carbon (3.5 g) were treated in a similar manner to that of Example 3 to give 7-[2-(tert-butoxycarbonylmethoxyimino)-2-(2-formamidothiazol-4-yl)acetamido]-3-methoxy-3-cephem-4-carboxylic acid (syn isomer, 3.8 g).

IR (Nujol): 3250, 1770, 1680, 1590, 1540 cm$^{-1}$.

NMR (DMSO-d$_6$, δ): 1.47 (9H, s), 3.63 (2H, s), 3.78 (3H, s), 4.65 (2H, s), 5.18 (1H, d, J=5 Hz), 5.62 (1H, d,d, J=5.8 Hz), 7.53 (1H, s), 8.53 (1H, s), 9.56 (1H, d, J=8 Hz).

EXAMPLE 5

Methanol (15 ml) and conc. hydrochloric acid (0.8 g) were added to 7-[2-(tert-butoxycarbonylmethoxyimino)-2-(2-formamidothiazol-4-yl)acetamido]-3-chloro-3-cephem-4-carboxylic acid (syn isomer, 2.2 g), and stirred at room temperature for 2.5 hours. To the resultant solution were added ethyl acetate (50 ml) and water (50 ml), and then the solution was adjusted to pH 7.5 with a saturated solution of sodium bicarbonate. After separating the aqueous layer, the aqueous solution was saturated with sodium chloride, and adjusted to pH 3.0 with 10% hydrochloric acid. After adding water, the solution was extracted with ethyl acetate. The extract was washed with a saturated solution of sodium chloride, dried over magnesium sulfate and concentrated in vacuo. The residue was triturated with diisopropyl ether and the precipitates were collected by filtration and dried to give 7-[2-(tert-butoxycarbonylmethoxyimino)-2-(2-aminothiazol-4-yl)acetamido]-3-chloro-3-cephem-4-carboxylic acid (syn isomer, 1.72 g).

IR (Nujol): 1770, 1720, 1660, 1610 cm$^{-1}$.

NMR (DMSO-d$_6$, δ): 1.44 (9H, s), 3.84 (2H, q, J=18.0 Hz), 4.58 (2H, s), 5.29 (1H, d, J=5.0 Hz), 5.85 (1H, dd, J=5.0 Hz, 8.0 Hz), 6.80 (1H, s), 7.27 (2H, broad-s), 9.57 (1H, d, J=8.0 Hz).

EXAMPLE 6

7-[2-(tert-butoxycarbonylmethoxyimino)-2-(2-formamidothiazol-4-yl)acetamido]-3-methoxy-3-cephem-4-carboxylic acid (syn isomer, 3.7 g), methanol (40 ml) and conc. hydrochloric acid (2.1 ml) were treated in a similar manner to that of Example 5 to give 7-[2-(tert-butoxycarbonylmethoxyimino)-2-(2-aminothiazol-4-yl)acetamido]-3-methoxy-3-cephem-4-carboxylic acid (syn isomer, 2.8 g).

IR (Nujol): 3350–3150, 1760, 1720 (shoulder), 1670, 1620, 1530 cm$^{-1}$.

NMR (DMSO-d$_6$, δ): 1.45 (9H, s), 3.6 (2H, s), 3.78 (3H, s), 4.58 (2H, s), 5.15 (1H, d, J=5 Hz), 5.57 (1H, d,d, J=5.8 Hz), 6.9 (1H, s), 9.43 (1H, d, J=8 Hz).

EXAMPLE 7

Methylene chloride (3.0 ml), anisole (1.6 ml) and trifluoroacetic acid (6.4 ml) were added to 7-[2-(2-tert-butoxycarbonylmethoxyimino)-2-(2-aminothiazol-4-yl)acetamido]-3-chloro-3-cephem-4-carboxylic acid (syn isomer, 1.6 g), and stirred at room temperature for 1.5 hours. To the resultant solution was added diisopropyl ether and triturated. The precipitates were collected by filtration and washed with diisopropyl ether. After water and ethyl acetate were added to the residue, the solution was adjusted to pH 7.5 with a saturated solution of sodium bicarbonate and the aqueous solution was separated. The aqueous solution was washed with ethyl acetate, and adjusted to pH 2.2 with diluted hydrochloric acid. The precipitates were collected by filtration, washed with water and dried over phosphorous pentoxide to give 7-[2-carboxymethoxyimino-2-(2-aminothiazol-4-yl)acetamido]-3-chloro-3-cephem-4-carboxylic acid (syn isomer, 0.71 g).

IR (Nujol): 3250, 1770, 1660 cm$^{-1}$.

NMR (DMSO-d$_6$, δ): 3.86 (2H, q, J=18.0 Hz), 4.63 (2H, s), 5.29 (1H, d, J=4.5 Hz), 5.86 (1H, dd, J=4.5 Hz, 8.0 Hz), 6.83 (1H, s), 9.59 (1H, d, J=8.0 Hz).

EXAMPLE 8

7-[2-(2-tert-butoxycarbonylmethoxyimino)-2-(2-aminothiazol-4-yl)acetamido]-3-methoxy-3-cephem-4-carboxylic acid (syn isomer, 2.7 g), methylene chloride (10 ml), anisole (2.2 g) and trifluoroacetic acid (12 g) were treated in a similar manner to that of Example 7 to give 7-[2-carboxymethoxyimino-2-(2-aminothiazol-4-yl)acetamido]-3-methoxy-3-cephem-4-carboxylic acid (syn isomer, 1.1 g).

IR (Nujol): 1760, 1660 cm$^{-1}$.

NMR (DMSO-d$_6$, δ): 3.67 (2H, s), 3.83 (3H, s), 4.73 (2H, s), 5.20 (1H, d, J=5 Hz), 5.62 (1H, d,d, J=5, 8 Hz), 7.05 (1H, s), 9.60 (1H, d, J=8 Hz).

What we claim is:

1. A compound selected from the group consisting of:
    4-nitrobenzyl 7-[2-(tert-butoxycarbonylmethoxyimino)-2-(2-formamidothiazol-4-yl)acetamido]-3-chloro-3-cephem-4-carboxylate (syn isomer), 7-[2-(tert-butoxycarbonylmethoxyimino-2-(2-formamidothiazol-4-yl)-acetamido]-3-chloro-3-cephem-4-carboxylic acid (syn isomer), 7-[2-(tert-butoxycarbonylmethoxyimino)-2-(2-aminothiazol-4-yl)-acetamido]-3-chloro-3-cephem-4-carboxylic acid (syn isomer), and 7-[2-carboxymethoxyimino-2-(2-aminothiazol-4-yl)acetamido]-3-chloro-3-cephem-4-carboxylic acid (syn isomer).

2. A compound of claim 1, which is 7-[2-carboxymethoxyimino-2-(2-aminothiazol-4-yl)acetamido]-3-chloro-3-cephem-4-carboxylic acid (syn isomer).

3. A pharmaceutical composition comprising an antimicrobially effective amount of a compound of claim 1 in association with a pharmaceutically acceptable, substantially non-toxic carrier or excipient.

* * * * *